(12) United States Patent
Roe et al.

(10) Patent No.: US 7,820,875 B2
(45) Date of Patent: Oct. 26, 2010

(54) DISPOSABLE ABSORBENT ARTICLES BEING ADAPTABLE TO WEARER'S ANATOMY

(75) Inventors: Donald Carroll Roe, West Chester, OH (US); Pankaj Nigam, Mason, OH (US); Mark James Kline, Okeana, OH (US); Jeromy Thomas Raycheck, Lebanon, OH (US); Carl Louis Bergman, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 974 days.

(21) Appl. No.: 10/811,696

(22) Filed: Mar. 29, 2004

(65) Prior Publication Data
US 2005/0215971 A1    Sep. 29, 2005

(51) Int. Cl.
*A61F 13/15* (2006.01)
(52) U.S. Cl. .................. 604/378; 604/379; 604/380; 604/381; 604/382; 604/383
(58) Field of Classification Search ............ 604/378, 604/379, 380, 381, 382, 383; 428/131–140, 428/170–172
See application file for complete search history.

(56) References Cited

U.S. PATENT DOCUMENTS

| | | |
|---|---|---|
| 3,848,594 A | 11/1974 | Buell |
| 3,860,003 A | 1/1975 | Buell |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A * | 9/1987 | Lawson ............... 604/385.27 |
| 4,699,622 A | 10/1987 | Toussant et al. |
| 4,834,735 A | 5/1989 | Alemany et al. |
| 4,846,815 A | 7/1989 | Scripps |
| 4,888,231 A | 12/1989 | Angstadt |
| 4,892,536 A | 1/1990 | DesMarais et al. |
| 4,894,060 A | 1/1990 | Nestegard |
| 4,940,464 A | 7/1990 | Van Gompel et al. |
| 4,946,527 A | 8/1990 | Battrell |
| 4,963,140 A | 10/1990 | Robertson et al. |
| 4,990,147 A | 2/1991 | Freeland |
| 5,037,416 A | 8/1991 | Allen et al. |
| 5,092,861 A | 3/1992 | Nomura et al. |
| 5,137,537 A | 8/1992 | Herron et al. |

(Continued)

FOREIGN PATENT DOCUMENTS

WO    WO 92/22273    12/1992

(Continued)

*Primary Examiner*—Jacqueline F. Stephens
(74) *Attorney, Agent, or Firm*—Charles R. Ware

(57) ABSTRACT

Absorbent articles having a liquid permeable topsheet, a liquid impermeable backsheet, and an absorbent core disposed between said topsheet and said backsheet are disclosed. The backsheet has a physical variation along at least one axis, wherein said physical variation defines a first backsheet zone and a second backsheet zone, and at least one elastomeric element having at least one primary direction of stretch, said elastomeric element at least partially overlapping and joined to first and/or second backsheet zone, wherein a relaxed pathlength of said elastomeric element in the primary direction of stretch is less than a total pathlength of said backsheet in the region of overlap. The physical variation is a measurable difference as measured by a physical property selected from the group consisting of basis weight, thickness and density.

18 Claims, 12 Drawing Sheets

U.S. PATENT DOCUMENTS

| | | |
|---|---|---|
| 5,147,345 A | 9/1992 | Young et al. |
| 5,151,092 A | 9/1992 | Buell |
| 5,156,793 A | 10/1992 | Buell et al. |
| 5,167,897 A | 12/1992 | Weber et al. |
| 5,221,274 A | 6/1993 | Buell |
| 5,242,436 A | 9/1993 | Weil et al. |
| 5,246,433 A | 9/1993 | Hasse et al. |
| 5,260,345 A | 11/1993 | DesMarais et al. |
| 5,269,775 A | 12/1993 | Freeland et al. |
| 5,342,338 A | 8/1994 | Roe |
| 5,387,207 A | 2/1995 | Dyer et al. |
| 5,397,316 A | 3/1995 | LaVon et al. |
| 5,499,978 A | 3/1996 | Buell et al. |
| 5,507,736 A | 4/1996 | Clear et al. |
| 5,554,143 A | 9/1996 | Roe et al. |
| 5,554,144 A | 9/1996 | Roe et al. |
| 5,554,145 A | 9/1996 | Roe et al. |
| 5,556,394 A | 9/1996 | Roe et al. |
| 5,569,232 A | 10/1996 | Roe et al. |
| 5,569,234 A | 10/1996 | Buell et al. |
| 5,571,096 A * | 11/1996 | Dobrin et al. ............... 604/383 |
| 5,575,783 A | 11/1996 | Clear et al. |
| 5,580,411 A | 12/1996 | Nease et al. |
| 5,591,152 A | 1/1997 | Buell et al. |
| 5,650,222 A | 7/1997 | DesMarais et al. |
| 5,749,866 A | 5/1998 | Roe et al. |
| 5,865,823 A | 2/1999 | Curro |
| 5,876,391 A | 3/1999 | Roe et al. |
| 5,897,545 A | 4/1999 | Kline et al. |
| 5,904,673 A | 5/1999 | Roe et al. |
| 5,916,663 A | 6/1999 | Chappell et al. |
| 5,957,908 A | 9/1999 | Kline et al. |
| 6,004,306 A | 12/1999 | Robles et al. |
| 6,107,537 A | 8/2000 | Elder et al. |
| 6,120,487 A | 9/2000 | Ashton |
| 6,120,489 A | 9/2000 | Johnson et al. |
| 6,325,787 B1 | 12/2001 | Roe et al. |
| 6,432,098 B1 | 8/2002 | Kline et al. |
| 6,503,236 B1 | 1/2003 | Uitenbroek et al. |
| 6,552,245 B1 | 4/2003 | Roessler et al. |
| 6,585,713 B1 | 7/2003 | LeMahieu et al. |
| 6,605,070 B2 | 8/2003 | Ludwig et al. |
| 2003/0009143 A1 | 1/2003 | Ludwig et al. |
| 2003/0088228 A1 | 5/2003 | Desai et al. |
| 2003/0233082 A1 | 12/2003 | Kline et al. |

FOREIGN PATENT DOCUMENTS

| | | |
|---|---|---|
| WO | WO 95/16746 A1 | 6/1995 |

* cited by examiner

DISPOSABLE ABSORBENT ARTICLES BEING ADAPTABLE TO WEARER'S ANATOMY

FIELD OF THE INVENTION

The present invention relates to a disposable absorbent article having stretchable properties for sustained fit and conformity to the wearer's anatomy while also being adaptable to the varying three-dimensional nature of the wearer's anatomy.

BACKGROUND OF THE INVENTION

The major function of absorbent articles, such as disposable diapers and adult incontinent briefs, is to absorb and contain body exudates. One common mode of failure for such products occurs when body exudates leak out of the gaps between the article and the wearer's leg and/or waist to adjacent clothing because they are not immediately absorbed within the article. As such, contemporary absorbent articles typically contain stretchable materials in the waist, side and cuff regions to provide sustained fit and a good seal of the article to the wearer's body.

One known technique for providing such stretchable materials is the incorporation of strands, films or nonwoven fibrous webs made of elastomeric materials. Typically, such materials are stretchable in at least one, and possibly multiple, directions. However, because the films or webs are made entirely of elastomeric materials, they are relatively expensive. Furthermore, these materials tend to have more drag on skin surface, resulting in discomfort to the wearer of the article. In some selected approaches, these stretchable strands or films are laminated to one or more substrate layers, such as nonwoven webs, plastic films, or nonwoven/film composites. Since these substrates typically are made of thermoplastic materials, they have very limited stretchability and are relatively stiff. Consequently, these laminated structures provide considerable resistance to stretch and/or conformity to a wearer's geometry. This conformity deficiency is compounded by the uniformity of these laminates, thus making them unable to adapt to the varying three-dimensional nature of the wearer's anatomy.

Another known technique for providing such stretchable materials is the incorporation of stretch-bonded laminates and neck-bonded laminates. Stretch-bonded laminates are made by stretching an elastic strand in the machine direction (MD), laminating it to a nonwoven substrate while it is in the stretched state, and releasing the applied tension so that the nonwoven gathers and takes on a puckered shape. Whereas, neck-bonded laminates are made by first stretching the nonwoven substrate in the machine direction such that it necks (i.e., reduces its cross direction (CD) dimension), then bonding CD oriented elastic strands to the substrate while the substrate is still in the stretched, necked state. Thus, the neck-bonded laminate will be stretchable in the CD, at least up to the original width of the nonwoven before it was necked. In some selected approaches, a combination of stretch-bonding and neck-bonding techniques are used to deliver stretch in both MD and CD directions. In this combined approach, at least one of the components is in a tensioned (i.e., stretched) state when the components of the laminates are joined together. While this combined approach provides multi-directional stretchability, the uniformity of these combined laminates is unable to adapt to the varying three-dimensional nature of the wearer's anatomy.

Yet another known technique for providing such stretchable materials is the incorporation of zero strain stretch laminates. Zero strain stretch laminates are made by bonding an elastomer to a nonwoven while both are in an unstrained state. These laminates are then incrementally stretched to impart the stretch properties. These incrementally stretched laminates are stretchable only to the extent afforded by the non-recovered (i.e., residual) extensibility of the laminate. For example, U.S. Pat. No. 5,156,793 discloses a method for incrementally stretching an elastomer-nonwoven laminate, in a non-uniform manner, to impart elasticity to the resulting laminate. While this approach may provide non-uniform stretchability, this non-selectable stretch does not adequately adapt to the varying three-dimensional nature of the wearer's anatomy.

What is needed is an absorbent article having stretchable properties for sustained fit and conformity to the wearer's anatomy while also being adaptable to the varying three-dimensional nature of the wearer's anatomy. More specifically, said absorbent article should be properly shaped and/or sized to the wearer for better fit, comfort, and wearer appearance, yet have the ability to maintain the required tension when on a wearer to achieve sustained fit and prevent sagging and/or drooping of the article. For example, said absorbent article should provide better shaping (i.e., contouring) of the buttocks and/or waist region. In the case of a diaper, better fit and comfort can also impart better functional performance such as reduced leakage since the diaper would better conform to the shape of a wearer.

SUMMARY OF THE INVENTION

A unitary disposable absorbent article comprising an absorbent core having a garment-facing surface and a body-facing surface, a liquid permeable topsheet positioned adjacent said body-facing surface of said absorbent core, a liquid impermeable backsheet positioned adjacent said garment-facing surface of said absorbent core, said backsheet having a physical variation in at least the central region of the backsheet along and overlapping at least the longitudinal axis, wherein said physical variation defines a first backsheet zone and a second backsheet zone, and at least one elastomeric element having at least one primary direction of stretch, said elastomeric element at least partially overlapping and joined to said second backsheet zone, wherein a relaxed pathlength of said elastomeric element in the primary direction of stretch is less than a total pathlength of said backsheet in the region of overlap. The physical variation is a measurable difference as measured by a physical property selected from the group consisting of basis weight, thickness and density. The physical variation is such that said second backsheet zone has a lower value than said first backsheet zone.

The absorbent article further comprises a front waist region, a back waist region, a crotch region and, optionally, a buttocks region. The backsheet zones may be positioned in one or more of said regions. The absorbent article may further comprise a third backsheet zone which may be positioned in one or more regions. The absorbent article may further comprise a second elastomeric element which may be positioned in one or more backsheet zones. The first and/or second elastomeric elements may be linear or non-linear (e.g., substantially u-shaped, etc.).

The absorbent article may be a disposable diaper (e.g., pant, non-preformed diaper), catamenial, adult incontinence product, or any other like product.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

Figure 1:
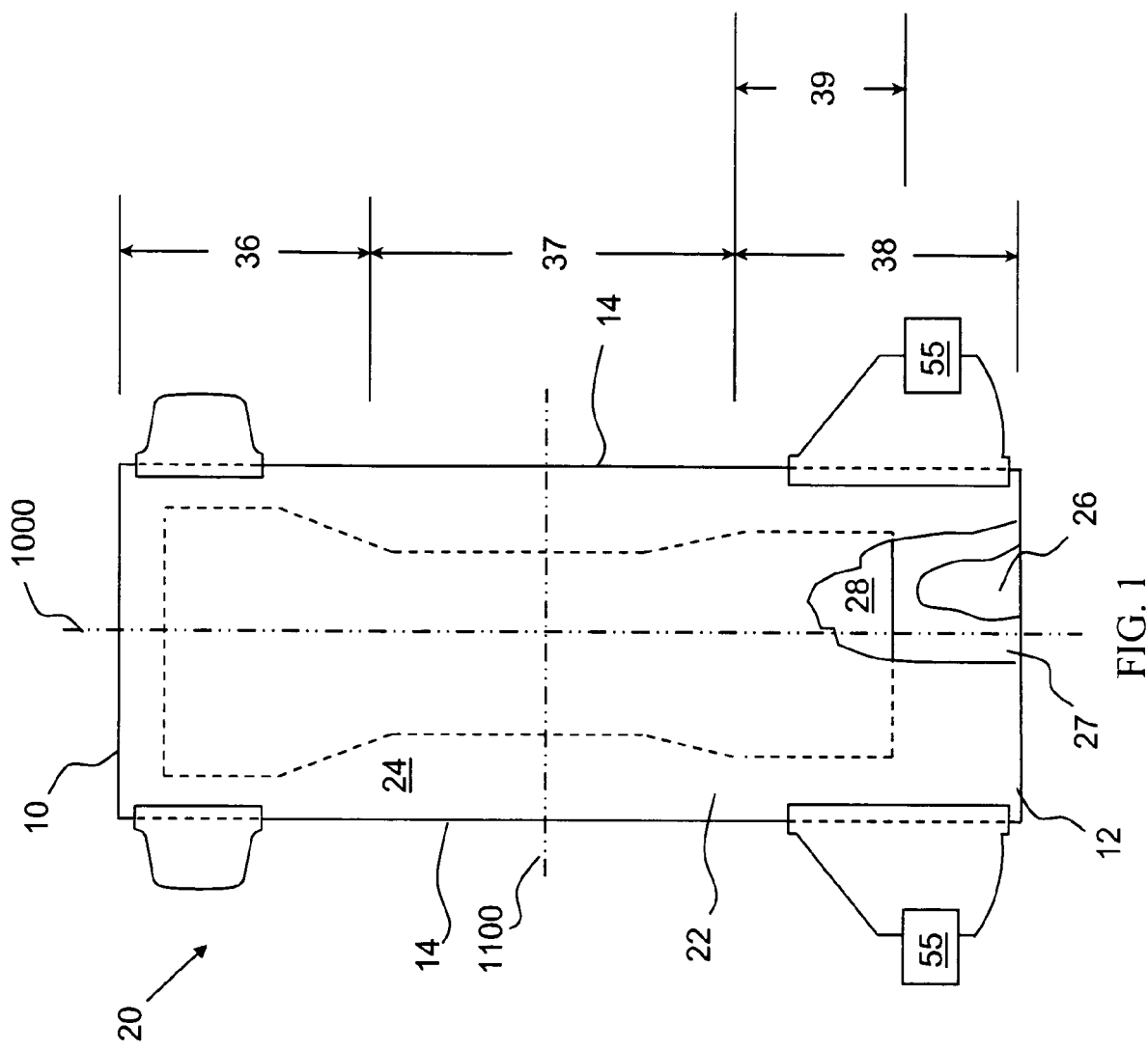
FIG. 1 is a plan view of an exemplary, non-limiting general embodiment of a diaper in accordance with the invention.

As used herein, the following terms have the following meanings:

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

The term "disposed" is used to mean that an element(s) is formed (joined and positioned) in a particular place or position as a unitary structure with other elements or as a separate element joined to another element.

The term "joined" encompasses configurations whereby an element is directly secured to another element by affixing the element directly to the other element, and configurations whereby an element is indirectly secured to another element by affixing the element to intermediate member(s) which in turn are affixed to the other element.

The term "unitary" absorbent article refers to absorbent articles which are formed of separate parts united together to form a coordinated entity so that they do not require separate manipulative parts like a separate holder and liner.

The term "diaper" refers to an absorbent article generally worn by infants and incontinent persons about the lower torso.

The term "stretch" means that a material has the ability to extend beyond its original length in at least one dimension when subjected to a tensile force (i.e., tension) applied in the direction of that dimension. "Stretch" may be unidirectional, bi-directional, or multi-directional. The specific "stretch" properties of a material may vary along any of the stretch vectors. As used herein, stretch includes both plastic and elastic deformation.

The terms "elastic" or "elasticity" mean that a material has the ability to return to less than 120% of its original pre-stretched dimension after an elongation-relaxation cycle such as subjecting it to tension or a force in that dimension and then releasing the elongating tension on the material (i.e., allowing the material to relax).

The term "elastic resistive force" describes an elastic force that tends to resist an applied tensile force. Further, said elastic force causes a material to tend to contract to an untensioned configuration. Elastic resistive force may be conveniently measured according to the methods described in Edana: Tensile Strength 20.2-89, wherein the elastic resistive force is measured when the material sample is stretched to 25% elongation.

The term "longitudinal" refers to a direction running parallel to the maximum linear dimension of the article and includes directions within ±45° of the longitudinal direction. The "lateral" or "transverse" direction is orthogonal to the longitudinal direction. The "Z-direction" is orthogonal to both the longitudinal and transverse directions. The "x-y plane" refers to the plane congruent with the longitudinal and transverse directions.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "vapor-permeable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The term "substrate" refers to any material, including a film, an apertured film, a nonwoven web, a woven web, a foam or a combination thereof, or a cellulosic material including wood pulp, derivatized or modified cellulosic materials, and the like, having a single layer or multiple layers. The term "fibrous substrate" as used herein refers to a material comprised of a multiplicity of fibers that could be either a natural or synthetic material or any combination thereof, including, for example, nonwoven materials, woven materials, knitted materials, and any combinations thereof.

The term "nonwoven" refers to a fabric made from continuous filaments and/or discontinuous fibers. Nonwoven fabrics include those made by carding staple fibers, airlaying or wet laying staple fibers and via extrusion processes such as spunbonding and melt blowing. The nonwoven fabric can comprise one or more nonwoven layers, wherein each layer can include continuous filaments or discontinuous fibers. Nonwovens can also comprise bi-component fibers, which can have shell/core, side-by-side, or other known fiber structures.

The term "pathlength" refers to a measurement along the topographic surface of the region in question in a direction substantially parallel to an axis. For example, when characterizing a stretch zone, a relaxed path length of the elastomeric element is measured and the total pathlength (i.e., total surface length along the 2D gathered topographic path) of the backsheet zone is measured. A method for determining the pathlength (i.e., surface-pathlength) of the respective regions can be found in the Test Methods section set forth in U.S. Pat. No. 5,916,663, entitled "Web materials exhibiting elastic-like behavior", issued to Chappell et al. on Jun. 29, 1999.

FIG. 1 is a plan view of an exemplary, non-limiting general embodiment of a diaper 20 of the present invention in its flat-out, uncontracted state (i.e., without elastic induced contraction) with portions of the structure being cut away to more clearly show the underlying structure of the diaper 20 and with the portion of the diaper 20 which contacts the wearer shown facing the viewer. The diaper 20 includes a longitudinal axis 1000 and a lateral axis 1100. One end portion 36 of the diaper 20 is configured as a front waist region 36 of the diaper 20. The opposite end portion 38 is configured as a back waist region 38 of the diaper 20. An intermediate portion 37 of the diaper 20 is configured as a crotch region 37, which extends longitudinally between the front and back waist regions 36 and 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer. Another optional intermediate portion 39 of the diaper 20 is configured as a buttocks region, which may be located in or near the proximal end of back waist region 38 as shown, or alternatively may overlap the crotch region 37 and back waist region 38. The outer periphery of diaper 20 is defined by longitudinal edges 14 and end edges 10, 12 which are located along the front and back waist region 36, 38, respectively.

The chassis 22 of the diaper 20 comprises the main body of the diaper 20. The chassis 22 comprises an outer covering including a liquid permeable topsheet 24 and/or a liquid impermeable backsheet 26 and at least a portion of an absorbent core 28 encased between the topsheet 24 and the backsheet 26. For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease, et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

The topsheet 24 may be fully or partially elasticized or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which is incorporated by reference herein.

The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; U.S. Pat. No. 5,397,316 entitled "Slitted Absorbent Members For Aqueous Body Fluids Formed Of Expandable Absorbent Materials" issued to LaVon et al. on Mar. 14, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The backsheet 26 is generally that portion of the diaper 20 positioned adjacent the garment-facing surface of the absorbent core 28. Backsheet 26 prevents the exudates absorbed and contained therein from soiling articles that may contact the diaper 20, such as bed sheets and undergarments. In preferred embodiments, the backsheet 26 is substantially impermeable to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, IN and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. An exemplary, suitable backsheet is disclosed in U.S. Pat. No. 6,107,537 entitled "Disposable absorbent articles providing a skin condition benefit" issued to Elder et al on Aug. 22, 2000. Other suitable materials and/or manufacturing techniques may be used to provide a suitable backsheet 26 including, but not limited to, surface treatments, particular film selections and processing, particular filament selections and processing, etc. Each of these references is hereby incorporated by reference herein.

Backsheet 26 may also consist of more than one layer, as exampled in FIG. 1, wherein a backsheet outer layer 26 (often referred to as the backsheet) may be made of a soft, nonwoven material and a backsheet inner layer 27 may be made of a substantially impermeable film. Adhesive 29, or any other suitable material or method, may be used to join layers 26 and 27 together. One known method for attaching these materials is to apply adhesive in a continuous striped pattern, discontinuous striped pattern or dot pattern. While a variety of backsheet configurations are contemplated herein, it would be obvious to those skilled in the art that various other changes and modifications can be made without departing from the spirit and scope of the invention.

The diaper 20 may also include a fastening system 55. The fastening system 55 preferably maintains the first waist region 36 and the second waist region 38 in a configuration so as to provide lateral tensions about the circumference of the diaper 20 to hold the diaper 20 on the wearer. The fastening system 55 preferably comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. No. 3,848,594 entitled "Tape Fastening System for Disposable Diaper" issued to Buell on Nov. 19, 1974; U.S. Pat. No. 4,662,875 B1 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. An exemplary interlocking fastening system is disclosed in co-pending U.S. Pat. No. 6,432,098 entitled "Absorbent Article Fastening Device" in the names of Kline et al. issued on Aug. 13, 2002. The fastening system 55 may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 entitled "Disposable Diaper Having An Improved Side Closure" issued to Toussant et al. on Oct. 13, 1987. to reduce shifting of overlapped portions or to improve fit as disclosed in U.S. Pat. No. 5,242,436 entitled "Absorbent Article With Fastening System Providing Dynamic Elasticized Waistband Fit" issued to Weil et al. on Sep. 7, 1993; U.S. Pat. No. 5,499,978 entitled "Absorbent Article With Dynamic Elastic Waist Feature Having A Predisposed Resilient Flexural Hinge" issued to Buell et al. on Mar. 19, 1996; U.S. Pat. No. 5,507,736 entitled "Absorbent Article With Dynamic Elastic Waist Feature Comprising An Expansive Tummy Panel" issued to Clear et al. on Apr. 16, 1996; U.S. Pat. No. 5,591,152 entitled "Absorbent Article With Dynamic Elastic Waist Feature Having A Predisposed Resilient Flexural Hinge" issued to Buell et al. on Jan. 7, 1997. Each of these patents and the co-pending application are incorporated herein by reference.

In alternative embodiments, the article may be preformed by the manufacturer to create a pant. The term "pant", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the term "pant" is used herein, pants are also commonly referred to as "closed diapers", "prefastened diapers", "pull-on diapers", "training pants" and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. patent application Ser. No. 10/171,249, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999, the disclosure of each of which is incorporated herein by reference.

Diaper 20 may also include such other features as are known in the art including cuffs, front and rear ear panels, waist cap features, a belt, elastics and the like to provide better fit, containment and aesthetic characteristics. Such additional features are well known in the art and are described in U.S. Pat. No. 3,860,003; and U.S. Pat. No. 5,151,092, which are incorporated by reference herein.

Diaper 20 is preferably applied to a wearer by positioning one of the waist regions under the wearer's back and drawing the remainder of the diaper between the wearer's legs so that the other waist region is positioned across the front of the wearer. The fastening elements 55 are then used by the caregiver to join the front and rear waist regions so as to encircle the wearer's waist. The elasticized side panels will typically be extended and tensioned during this operation so as to conform to the size and shape of the wearer.

Figure 2:
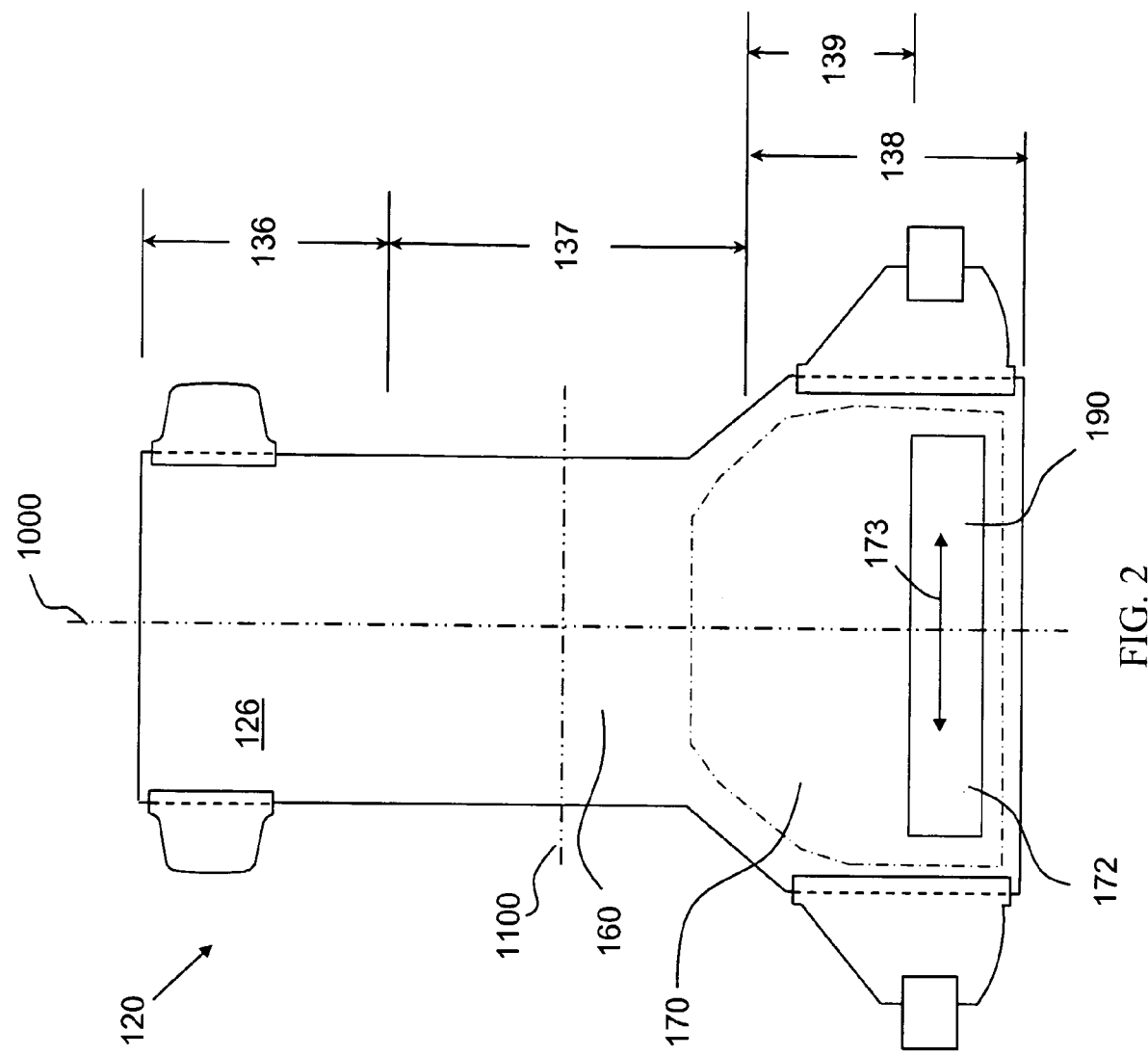
FIG. 2 is a plan view of an exemplary, non-limiting embodiment of a diaper in accordance with the invention.

FIG. 2 is a plan view of an exemplary, non-limiting embodiment of a diaper 120 of the present invention in its flat-out, uncontracted state (i.e., without elastic induced contraction) with the backsheet 126, which contacts the wearer's garment, shown facing the viewer. Backsheet 126 has at least two backsheet zones differing from each other in at least one of the following physical properties: basis weight, thickness, and density. For example, a second backsheet zone 170 has a lower value of one of said physical properties than does a first backsheet zone 160. Moreover, the ratio of said property in the second backsheet zone 170 to the value of the same property in the first backsheet zone 160 is less than about 0.8, more preferably less than about 0.7, and most preferably less than about 0.6. Typically, the ratio of the property in the second backsheet zone 170 to that in the first backsheet zone 160 is in the range of about 0.5 and about 0.8. Importantly, the physical property(ies) of the backsheet are measured when the backsheet is in a flat-out, extended state (i.e., not in a pleated, folded, wrinkled, or elastically gathered state) and carefully removed from the remainder of the article. In so doing, care must be taken not to destroy the sample or cause unintended gross deformation of any parts of the sample. The layers of the sample may be frozen to aid their separation from adjacent layers of the sample, when necessary. Freezing may be accomplished using PH100-15 circuit refrigerant made by Philips ECG, Inc. of Waltham, Mass. The average basis weight of a backsheet zone may be measured by weighing a known area of the backsheet zone and subsequently dividing the weight by the measured area. Alternatively, a sample cutting die may be used to ensure proper, consistent and predefined sample sizes. In so doing, the die cut may be made on one or more layers of the article so long as the backsheet is ultimately removed from the other layers. In this way, any subsequent deformation of the backsheet material prior to weighing is unimportant as the basis weight of the original sample is equal to the sample weight divided by the area of the predefined cut area (i.e., original sample size). Lastly, and hereinafter applicable, said physical properties may be calculated as an average of multiple measurements, when appropriate. The backsheet zones of the present invention described herein are preferably located primarily in the central portion of the diaper, overlapping the longitudinal axis of the diaper.

A lower basis weight, thickness or density of the second backsheet zone 170 may be achieved by any known suitable techniques including, but not limited to, partial plastic deformation (e.g., stretching) of said second backsheet zone in at least one of a length and width dimension. For example, said stretching may be performed by a process commonly referred to as ring-rolling, as described in U.S. Pat. No. 5,167,897, entitled "Method for incrementally stretching a zero strain stretch laminate web to impart elasticity thereto" to Weber et al on Dec. 1, 1992. The depth of engagement of the ring-roll may be varied along the longitudinal axis 1000 of the backsheet 126 in order to produce the differing first and second backsheet zones.

The above-mentioned method of stretching the backsheet material may be achieved by any suitable technique including, but not limited to, using pitched or non-pitched ring rolls having mating and interpenetrating teeth. In either case, the teeth may engage the material at different depths of engagement along the width and/or length of the material to provide different zones of stretch. Typically, said engagement imparts an applied strain between 0% and 200% to the material.

In the case of pitched activation, for example, the changing depth of engagement may be accomplished by having the mating rolls machined to different circumferences such that their teeth engage at different depths. In the case of non-pitched activation, for example, the rolls may be made to matching concentric diameters but their center-to-center distance may be changed to alter their depth of engagement. For instance, an upper roll may be driven downward to engage a lower roll, but the upper roll may be raised (e.g., by a cam against roll shaft) in a periodic manner to alter the depth of engagement.

When stretching the material, holes in said material are often undesirable. One known technique for minimizing the number of unwanted holes is to control the strain rate (e.g., less than 800 sec-1, more preferably less than 300 sec-1). The strain rate may be controlled by controlling roll speed and diameter. Additionally, holes may result when adhesive is applied in an area that spans two or more adjacent activation teeth. More specifically, the adhesive may be strained to failure, thus resulting in a high strain rate release that causes holes in the adjacent material. One known technique to minimize adhesive failure is to apply said adhesive in a discontinuous fashion such that it does not span two or more adjacent activation teeth. Another known technique is to apply heat (e.g., above 40 degrees Celsius, or more preferably above 50 degrees Celsius) to said adhesive prior to or during the stretch process to cause it to be more fluid and less brittle.

Regardless of the stretching method employed, incorporating differing backsheet zones allows for various shaping of the absorbent article 120 in light of the varying three-dimensional nature of the wearer's anatomy. For example, second backsheet zone 170 is more conformable about the wearer because of its lower value of one of said physical properties. Furthermore, second backsheet zone 170 provides better coverage of the wearer's anatomy in its stretched state. Consequently, second backsheet zone is better suited to conform about the wearer, for example, the buttocks region 39 where the wearer's body protrudes the most. Conversely, first backsheet zone 160 need not be as conformable in order to adapt to the wearer in the crotch region 37 and front waist region 36.

In certain preferred embodiments, the second backsheet zone overlaps the back portion of the absorbent core. In these embodiments, the portion of the second backsheet zone overlapping the core is preferably either not bonded to the core or is bonded only in a narrow region along the longitudinal axis of the article. The area of bonding between the absorbent core and the second backsheet zone is preferably less than half the area of overlap. In other preferred embodiments, the second backsheet zone does not extend completely to the back lateral edge of the article (i.e., the total pathlength of the backsheet at the back lateral edge of the article is less than the total pathlength of the backsheet in the second backsheet zone).

Additionally, in accordance with the present invention, an elastomeric element 190 may be applied to backsheet 126 to provide sustained fit and conformity to the wearer's body. Elastomeric element 190 may be joined to backsheet 126 in an area at least partially overlapping the second backsheet zone 170 and preferably overlapping the longitudinal axis of the article. Preferably, the relaxed pathlength of elastomeric element 190 is shorter than the total pathlength of backsheet 126 within the second backsheet zone 170 in their area of joining. For example, the ratio of the relaxed pathlength of elastomeric element 190 to the total pathlength of backsheet 126 within the second backsheet zone 170 in the joined area is less than about 0.8, more preferably less than about 0.7, and most preferably less than about 0.6. Importantly, the difference between these pathlengths defines the maximum elongation of the stretch zone. The elastomeric element may be elongated up to the total pathlength of the backsheet in the stretch zone area with only minimal resistance from the backsheet. However, once the elastomeric element is elongated to the total backsheet pathlength, significant resistance to further elongation is provided by the backsheet material (i.e., the backsheet acts to provide a "force wall" to prevent further significant elongation under the forces normally encountered in a wearable absorbent article). Additionally, the pathlength of the topsheet 24 may be shorter than the pathlength of the backsheet 126 to provide an additional force wall. This phenomenon is important to prevent sagging of the article once loaded by the wearer's waste or stressed by the wearer's physical activity. Additionally, in preferred embodiments, the force to elongate the stretch zone a given proportion is less than the force required to elongate one of the stretch ears or side panels proportionately.

Elastomeric element 190 may be bonded in an unstretched state to backsheet 126 in the desired backsheet zone prior to the stretching (e.g., ring-rolling) process. Elastomeric element 190 may be strained to approximately the same degree as backsheet 126 within the backsheet zone, in their area of overlap, during the stretching process. However, upon release of the straining tension, elastomeric element 190 relaxes to a smaller pathlength than that of backsheet 126 in the stretched area (i.e., the elastomeric element 190 recovers a greater percentage of the applied strain). Alternatively, elastomeric element 190 may be affixed to backsheet 126 or the topsheet in a pre-stretched condition either prior to, or subsequent to, the aforementioned stretching step. Suitable elastomeric elements include, but are not limited to, films, apertured films, strands, extruded strands, extruded elastomers, slot coated elastomeric adhesives, printed elastomers, scrims, foams, elastic nonwovens, and SELFed materials (as exampled in U.S. Pat. No. 5,916,663, supra). In preferred embodiments, the elastomeric element 190 is oriented in substantially the lateral direction and the backsheet stretching process extends the backsheet 126 in substantially the same direction, thus resulting in a primary stretch vector 173 of the stretch zone 172 oriented around the back waist of the wearer.

Where a backsheet zone (e.g., second backsheet zone 170) and an elastomeric element (e.g., elastomeric element 190) overlap, a stretch zone 172 is created. More specifically, for example, elastomeric element 190 is joined to an at least partially overlapping area of second backsheet zone 170 to form stretch zone 172. Thus, stretch zone 172 provides the combined functions of improved coverage, sustained fit and conformity to the varying three-dimensional geometries of the wearer's body. Stretch zone 172 may be characterized by measuring the relaxed pathlength of its elastomeric element 190 and by measuring the total pathlength of its second backsheet zone 170 as described above.

Typically, stretch zones have the following properties: (1) an elastic resistive force (i.e., a normalized load at 25% elongation) of at least about 0.03 N/cm, preferably from 0.03 N/cm to about 50 N/cm, more preferably from about 0.05 N/cm to about 40 N/cm, and most preferably from 0.25 n/cm to about 30 N/cm; 2) a percent set of less than about 25%, preferably less than about 15% and more preferably less than about 10%; and (3) a stress relaxation value of less than about 50%, preferably less than about 30%, and more preferably less than about 20%. Methods for measuring these properties are given in U.S. patent application Ser. No. 10/288,095, filed on Nov. 5, 2002 and published as US 2003/0088228A1.

Each stretch zone may have continuous or discontinuous properties in any direction wherein the varying properties include chemical composition, elasticity, extensibility, maximum elongation, other stress/strain properties, vectors or angles, basis weight, geometry, dimensions, 3-dimensional morphology, visual distinctiveness, and the like. A stretch zone may have continuous properties (e.g., elastomeric composition, substrate material and/or treatment have relatively homogeneous properties). Alternatively, stretch zones may have discontinuous properties due to provision of non-homogeneous properties thereto. In certain embodiments, at least a portion of at least one stretch zone may be visually distinct. In certain preferred embodiments, the stretch zone at least partially overlaps the region between the rear fasteners of the article so as to store elastic energy in a continuous line of tension to enhance the conformity and sustained fit of the article.

Figure 3:
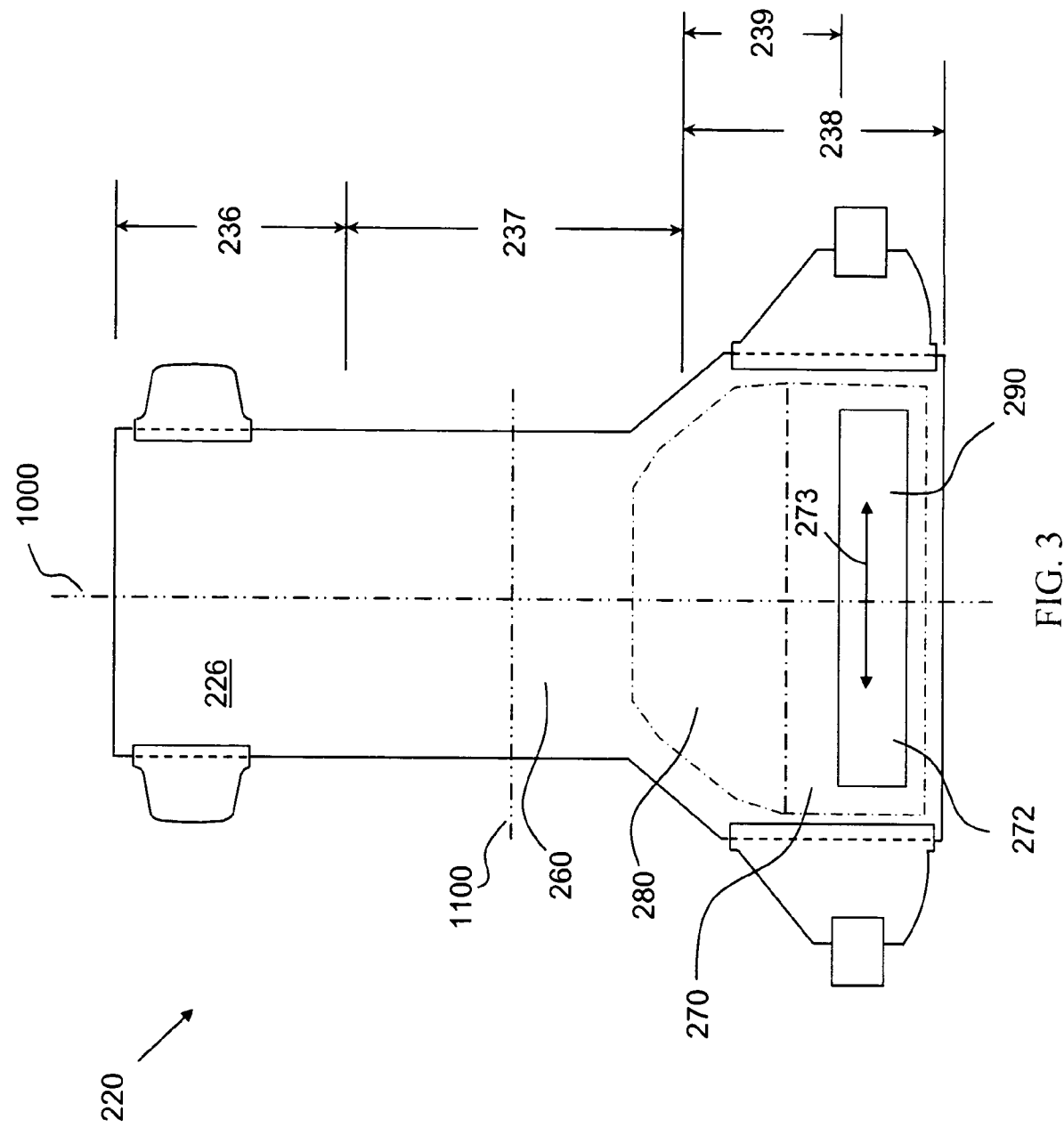
FIG. 3 is a plan view of another exemplary, non-limiting embodiment of a diaper in accordance with the invention.

FIG. 3 is a plan view of another exemplary, non-limiting embodiment of a diaper 220 of the present invention in its flat-out, uncontracted state (i.e., without elastic induced contraction) with the backsheet 226, which contacts the wearer's garment, shown facing the viewer. Similar to FIG. 2, diaper 220 has a first backsheet zone 260 and a second backsheet zone 270. Additionally, diaper 220 has a third backsheet zone 280. First backsheet zone 260 is disposed primarily in the crotch region 237 and front waist region 236. Second backsheet zone 270 is disposed primarily in the distal portion of back waist region 238. Third backsheet zone 280 is disposed longitudinally inboard of the second backsheet zone 270 (e.g., primarily in the buttocks region 239). Third backsheet zone 280 has a lower basis weight, thickness, or density than second backsheet zone 270 which has a lower basis weight, thickness, or density than first backsheet zone 260. Third backsheet zone 280 is designed to conform to the outward-protruding buttocks of the wearer. Diaper 220 also has an elastomeric element 290 which overlaps a portion of second backsheet zone 270 and is joined to the diaper in the overlapping, thus forming a stretch zone 272 having a primary direction of stretch in the lateral direction as indicated by arrow 273. Stretch zone 272 may be characterized by measuring the relaxed path length of its elastomeric element 290 and by measuring the total pathlength of its second backsheet zone 270 as described herein. Stretch zone 272 (i.e., second backsheet zone 270 combined with elastomeric element 290) is located near the distal portion of back waist region 238 so as to anchor the diaper 220 to the lower back region of the wearer, discussed infra. As exampled in this embodiment, not all backsheet zones (herein third backsheet zone 280) overlap an elastomeric element. While third backsheet zone 280 does not provide elastic recovery to the diaper 220, it may function to cover and conform to the wearer's anatomy and to bear tensions or loads associated with the anatomy or motion of the wearer, or the diaper or contents thereof, e.g., through the waist or buttocks region of the article, especially in regions where they are not affixed to the absorbent core (not shown) or other thicker, more rigid elements of the diaper. As exampled, these zones may be discrete zones having different properties than the backsheet zone(s) comprising the stretch zone(s). Alternatively, these zones may comprise the portions of any of the backsheet zones not joined to an elastomeric element. Lastly, in a non-limiting example, the absorbent core (not shown) is either affixed to backsheet 226 in the third backsheet zone 280 along longitudinal centerline 1000 or not at all in the region where the backsheet zone overlaps the absorbent core. In another non-limiting example, the absorbent core (not shown) does not extend into the second backsheet zone 270.

Figure 4:
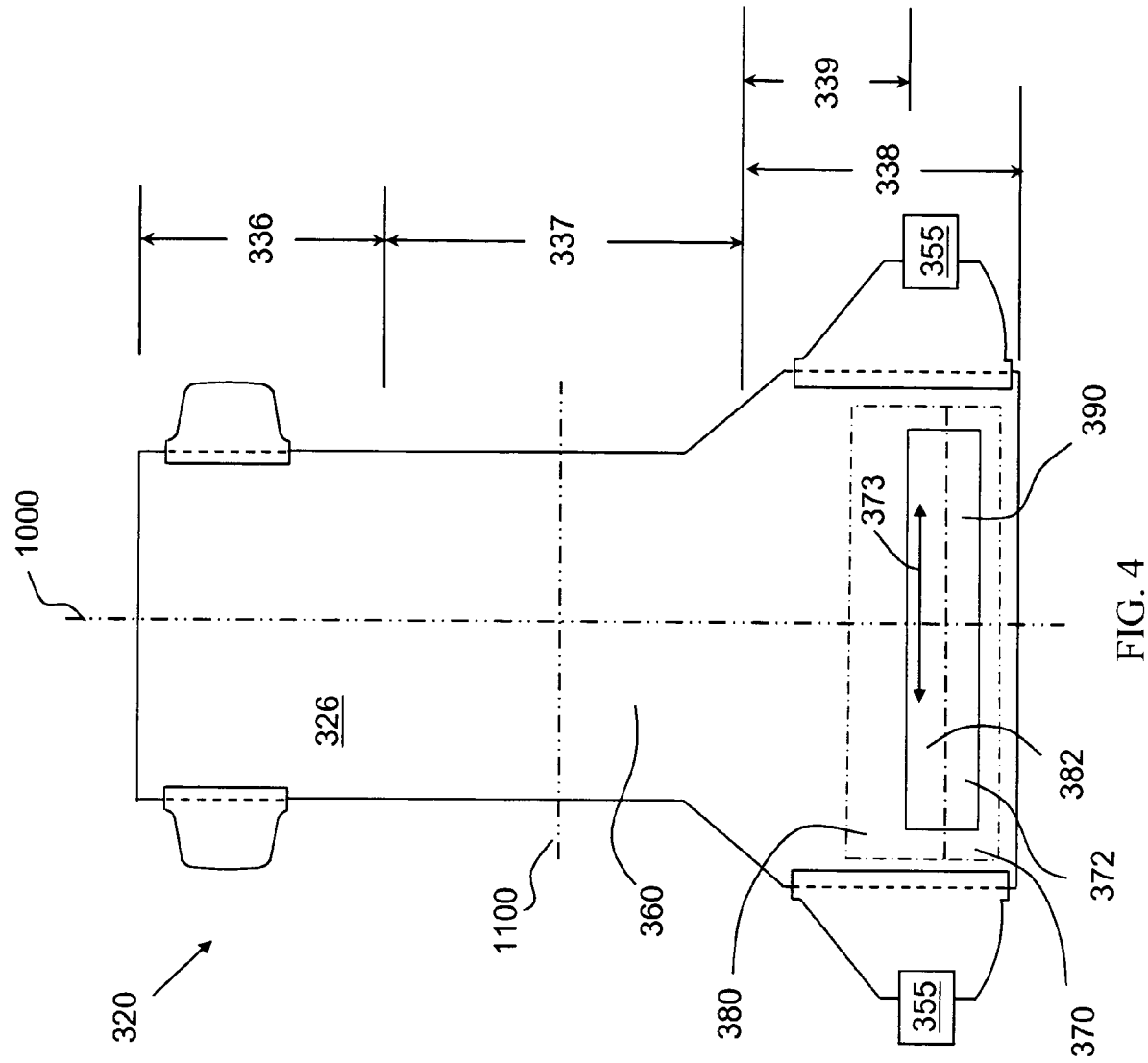
FIG. 4 is a plan view of yet another exemplary, non-limiting embodiment of a diaper in accordance with the invention.

FIG. 4 is a plan view of yet another exemplary, non-limiting embodiment of a diaper 320 of the present invention in its flat-out, uncontracted state (i.e., without elastic induced contraction) with the backsheet 326, which contacts the wearer's garment, shown facing the viewer. Similar to FIG. 3, diaper 320 has a first backsheet zone 360, a second backsheet zone 370 and a third backsheet zone 380. First backsheet zone 360 is disposed primarily in the crotch region 337 and front waist region 336. Second backsheet zone 370 is disposed primarily in the distal portion of back waist region 338. Third backsheet zone 380 is disposed primarily in the back waist region 338 with at least a portion extending into buttocks region 339. Third backsheet zone 380 has a lower basis weight, thickness, or density than second backsheet zone 370 which has a lower basis weight, thickness, or density than first backsheet zone 360. Third backsheet zone 380 is such designed to conform to the outward-protruding buttocks of the wearer. Diaper 320 also has an elastomeric element 390 which overlaps and is joined to a portion of second backsheet zone 370 and third backsheet zone 380, thus forming two discrete stretch zones 372, 382 having a primary direction of stretch in the lateral direction as indicated by arrow 373. In this way, only a single elastomeric element 390 is needed to create a first stretch zone 372 and a second stretch zone 382. Stretch zone 372 (i.e., second backsheet zone 370 combined with elastomeric element 390) is located near the distal portion of back waist region 338 so as to anchor the diaper 320 to the lower backside of the wearer, discussed infra. Stretch zone 382 (i.e., third backsheet zone 380 combined with elastomeric element 390) is located longitudinally inboard of stretch zone 372 and substantially, laterally-aligned with fastening elements 355. Being more extensible than stretch zone 372, stretch zone 382 facilitates the lateral pulling of fastening elements 355 by the wearer or caregiver particularly during application and the generation of a line of tension between the fastening elements; whereas, stretch zone 372 continues to provide anchoring within the back waist region 338 and prevents gapping at the back waist edge. In a non-limiting example, the absorbent core (not shown) is either affixed to backsheet 326 in the third backsheet zone 380 along longitudinal centerline 1000 or not at all. In another non-limiting example, the absorbent core (not shown) does not extend into the second backsheet zone 370.

Figure 5:
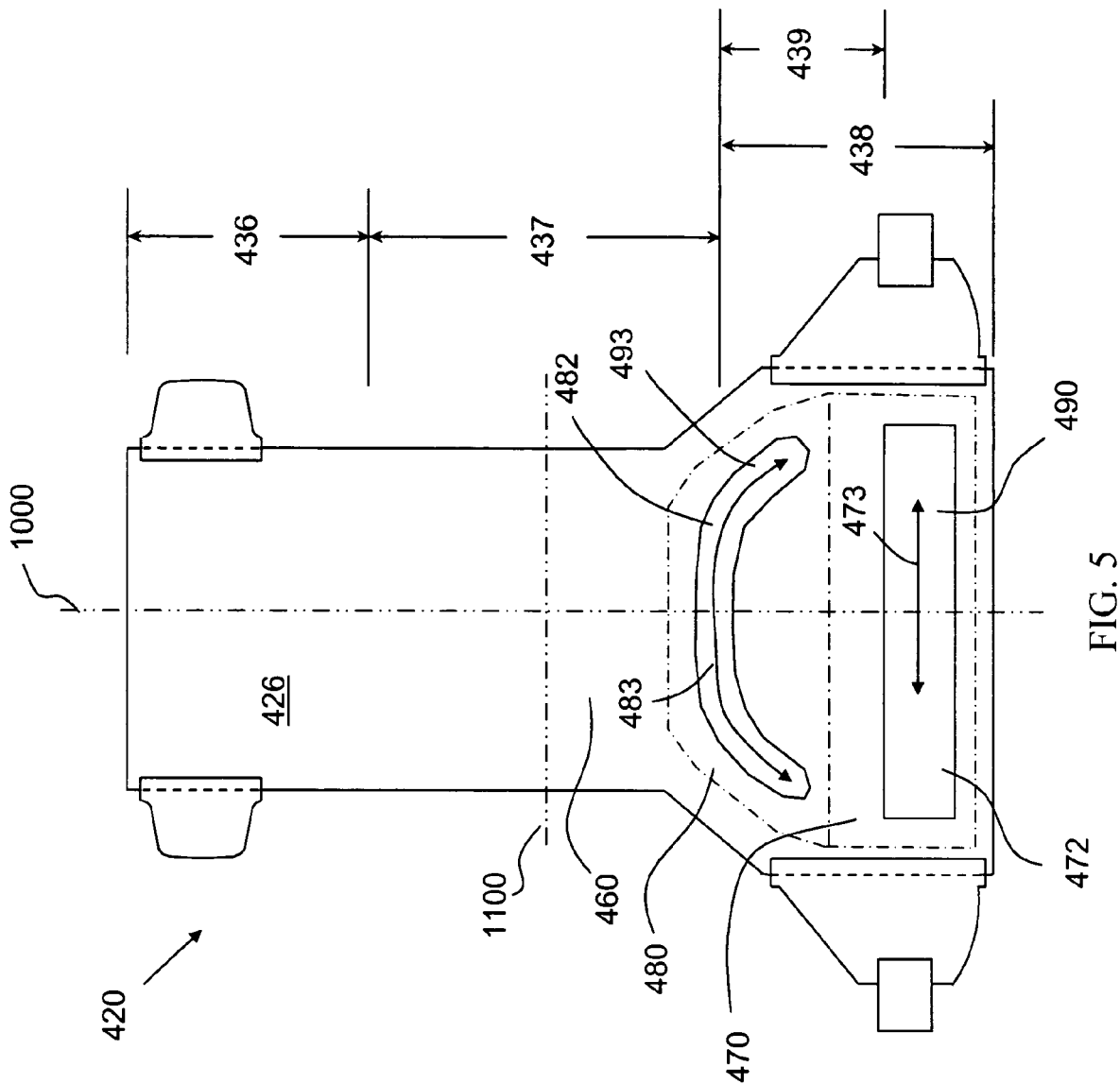
FIG. 5 is a plan view of yet another exemplary, non-limiting embodiment of a diaper in accordance with the invention.

FIG. 5 is a plan view of yet another exemplary, non-limiting embodiment of a diaper 420 of the present invention in its flat-out, uncontracted state (i.e., without elastic induced contraction) with the backsheet 426, which contacts the wearer's garment, shown facing the viewer. Similar to FIG. 3, diaper 420 has a first backsheet zone 460, a second backsheet zone 470 and a third backsheet zone 480. First backsheet zone 460 is disposed primarily in the crotch region 437 and front waist region 436. Second backsheet zone 470 is disposed primarily in the distal portion of back waist region 438. Third backsheet zone 480 is disposed primarily in the back waist region 438 with at least a portion extending into buttocks region 439. Third backsheet zone 480 has a lower basis weight, thickness, or density than second backsheet zone 470 which has a lower basis weight, thickness, or density than first backsheet zone 460. Third backsheet zone 480 is such designed to conform to the outward-protruding buttocks of the wearer. Diaper 420 also has a first elastomeric element 490 which overlaps and is joined to a portion of second backsheet zone 470, thus forming a first stretch zone 472 having a primary direction of stretch in the lateral direction as indicated by arrow 473. Additionally, diaper 420 has a second elastomeric element 493 which overlaps and is joined to a portion of third backsheet zone 480, thus forming a second stretch zone 482 having a primary direction of stretch in a non-linear (e.g., substantially u-shaped) configuration as indicated by arrow 483. In this way, two elastomeric elements 490, 493 are used to create a first stretch zone 472 and a second stretch zone 482, respectively. Stretch zone 472 (i.e., second backsheet zone 470 combined with elastomeric element 490) is located near the distal portion of back waist region 438 so as to anchor the diaper 420 to the lower backside of the wearer, discussed infra. Stretch zone 482 (i.e., third backsheet zone 480 combined with elastomeric element 490) is located longitudinally inboard of stretch zone 472 so as to provide contoured stretch within the buttocks region 439. In a non-limiting example, the absorbent core (not shown) is either affixed to backsheet 426 in the third backsheet zone 480 along longitudinal centerline 1000 or not at all. In another non-limiting example, the absorbent core (not shown) does not extend into the second backsheet zone 470.

Figure 6:
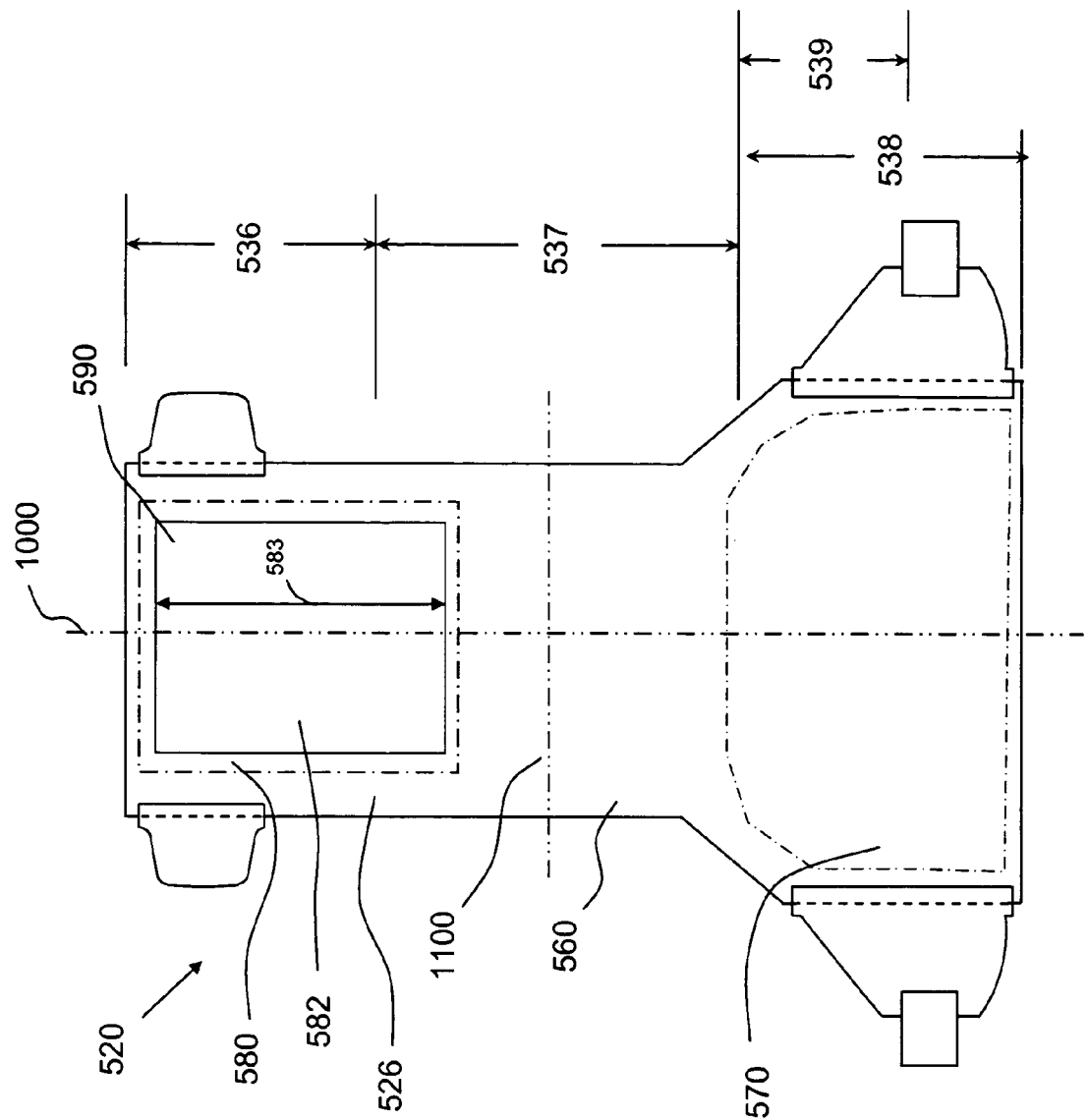
FIG. 6 is a plan view of yet another exemplary, non-limiting embodiment of a diaper in accordance with the invention.

FIG. 6 is a plan view of yet another exemplary, non-limiting embodiment of a diaper 520 of the present invention in its flat-out, uncontracted state (i.e., without elastic induced contraction) with the backsheet 526, which contacts the wearer's garment, shown facing the viewer. Similar to FIG. 3, diaper 520 has a first backsheet zone 560, second backsheet zone 570 and a third backsheet zone 580. First backsheet zone 560 is disposed primarily in the crotch region 537 and front waist region 536. Second backsheet zone 570 is disposed primarily in the back waist region 538. Third backsheet zone 580 is disposed primarily in the front waist region 536. Third backsheet zone 580 has a lower basis weight, thickness, or density than second backsheet zone 570 which has a lower basis weight, thickness, or density than first backsheet zone 560. Diaper 520 also has an elastomeric element 590 which overlaps and is joined to a portion of third backsheet zone 580, thus forming stretch zone 582 having a primary direction of stretch in the longitudinal direction as indicated by arrow 583. In this embodiment, one skilled in the art would recognize the desirability to stretch the backsheet in the longitudinal direction and that the pathlengths of the backsheet zone 580 and elastomeric element 590 should be measured in the longitudinal direction as well. Stretch zone 582 (i.e., third backsheet zone 580 combined with elastomeric element 590) is located in the front waist region 536 so as to facilitate the variable stretch during application of diaper 520 given the varying lengths of wearers'torsos. In a non-limiting example, the absorbent core (not shown) does not extend into the second backsheet zone 570. In a non-limiting example, the absorbent core (not shown) is not attached to the backsheet 526 in stretch zone 582. One skilled in the art should appreciate this particular embodiment may be practiced without the presence of the second backsheet zone 570 in the back waist region 560.

Figure 7:
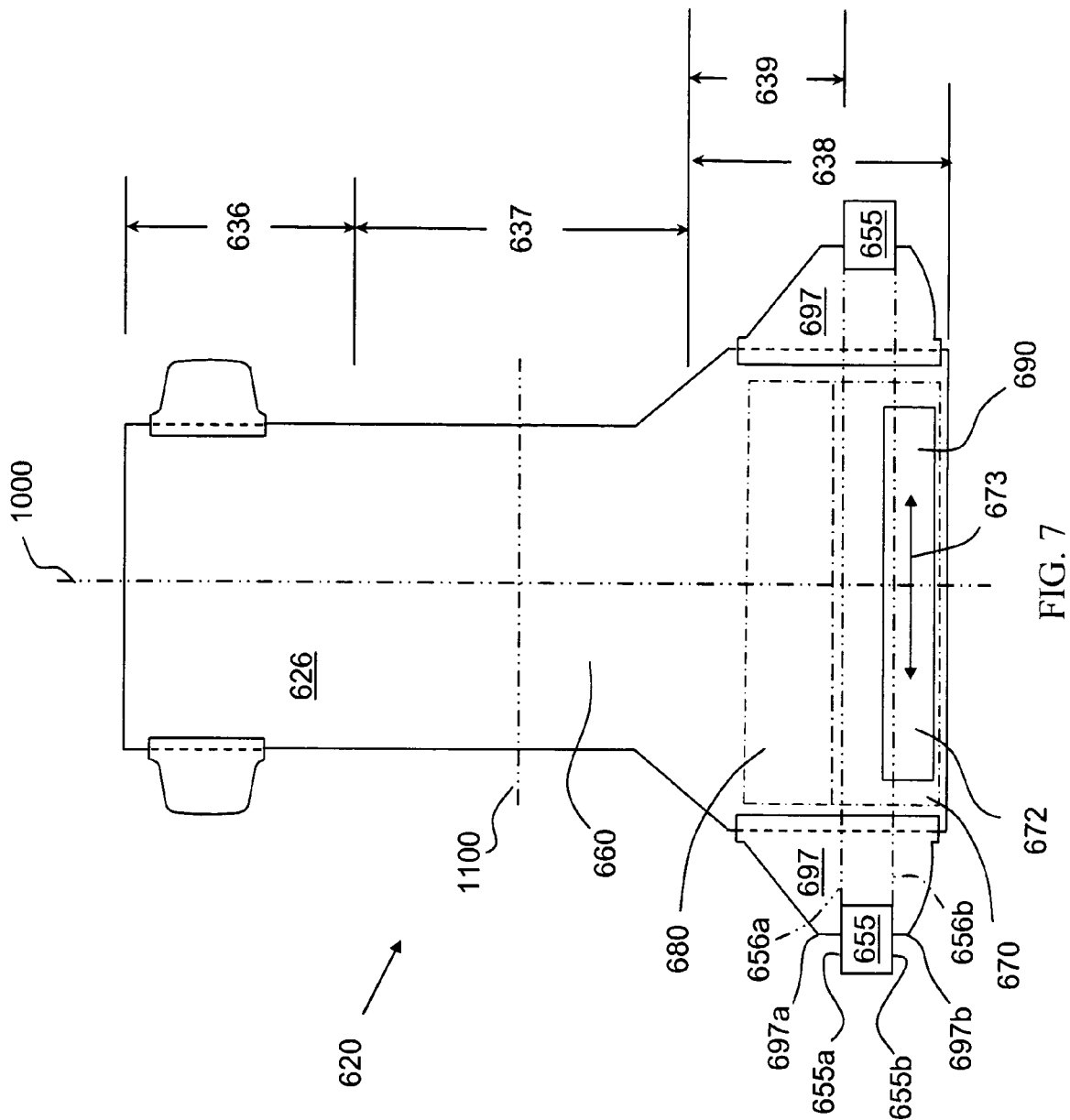
FIG. 7 is a plan view of yet another exemplary, non-limiting embodiment of a diaper in accordance with the invention.

FIG. 7 is a plan view of yet another exemplary, non-limiting embodiment of a diaper 620 of the present invention in its flat-out, uncontracted state (i.e., without elastic induced contraction) with the backsheet 626, which contacts the wearer's garment, shown facing the viewer. Similar to FIG. 3, diaper 620 has a first backsheet zone 660, a second backsheet zone 670 and a third backsheet zone 680. First backsheet zone 660 is disposed primarily in the crotch region 637 and front waist region 636. Second backsheet zone 670 is disposed primarily in the distal portion of back waist region 638. Third backsheet zone 680 is disposed primarily in the back waist region 638 with at least a portion extending into buttocks region 639. Third backsheet zone 680 has a lower basis weight, thickness, or density than second backsheet zone 670 which has a lower basis weight, thickness, or density than first backsheet zone 660. Third backsheet zone 680 is such designed to conform to the outward-protruding buttocks of the wearer. Diaper 620 also has an elastomeric element 690 which overlaps and is joined to a portion of second backsheet zone 670, thus forming discrete stretch zones 672 having a primary direction of stretch in the lateral direction as indicated by arrow 673. Stretch zone 672 (i.e., second backsheet zone 670 combined with elastomeric element 690) is located near the distal portion of back waist region 638 so as to anchor the diaper 620 to the lower backside of the wearer, discussed infra.

Stretch zone 672 may be preferably aligned with the ears 697 and/or fasteners 655 disposed on ears 697 in order to create a substantially continuous line of tension around the waist to promote conforming sustained fit. As shown in FIG. 7, stretch zone 672 preferably at least partially overlaps one of the two imaginary lines 656a and 656b that connect the longitudinally outboard edges 655a and 655b of either fasteners 655. In embodiments in which diaper 620 does not include fasteners 655, for example in diaper pant 720 of FIG. 8, imaginary lines 656a and 656b may connect the narrowest outboard point edges 697a and 697b of ears 697. In some embodiments, a stiffening member may be used to further distribute the elongation force throughout the ears 697. In such embodiments which include a stiffening element that is wider than the fastener (not shown), the separation of the imaginary lines is defined by the longitudinal length of the stiffening element.

In a non-limiting example, the absorbent core (not shown) is either affixed to backsheet 626 in the third backsheet zone 680 along longitudinal centerline 1000 or not at all. In another non-limiting example, the absorbent core (not shown) does not extend into the second backsheet zone 670.

Figure 8:
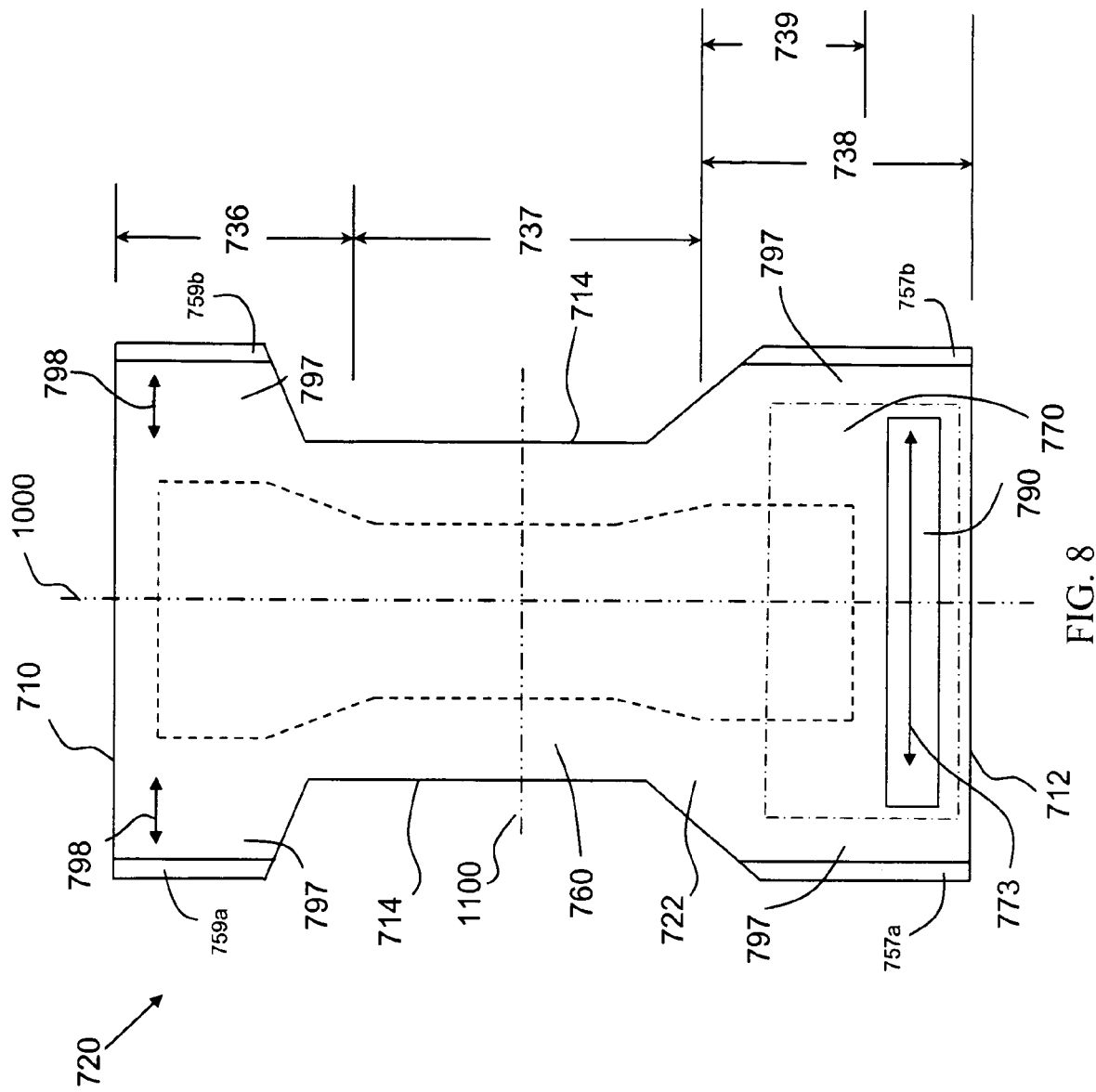
FIG. 8 is a plan view of an exemplary, non-limiting general embodiment of a pant in accordance with the invention.

FIG. 8 is a plan view of an exemplary, non-limiting embodiment of a pant 720 of the present invention in its flat-out, uncontracted, non-preformed state (i.e., without elastic induced contraction) with portions of the structure being cut away to more clearly show the underlying structure of the diaper 720 and with the portion of the diaper 720 which contacts the wearer shown facing the viewer. The diaper 720 includes a longitudinal axis 1000 and a lateral axis 1100. One end portion 736 of the diaper 720 is configured as a front waist region 736 of the diaper 720. The opposite end portion 738 is configured as a back waist region 738 of the diaper 720. An intermediate portion 737 of the diaper 720 is configured as a crotch region 737, which extends longitudinally between the front and back waist regions 736 and 738. The waist regions 736 and 738 generally comprise those portions of the diaper 720 which, when worn, encircle the waist of the wearer. The waist regions 736 and 738 may include elastic elements such that they gather about the waist of the wearer to provide improved fit and containment. The crotch region 737 is that portion of the diaper 720 which, when the diaper 720 is worn, is generally positioned between the legs of the wearer. Another intermediate portion 739 of the diaper 720 is configured as a buttocks region, which is located in or near the proximal end of back waist region 738. The outer periphery of diaper 720 is defined by longitudinal edges 714 and end edges 710, 712 which are located along the front and back waist region 736, 738, respectively. First connection zones 757a, 757b are attached to second connection zones 759a, 759b, respectively, prior to being purchased by the consumer (e.g., prior to being packaged) as exampled in FIG. 8. Diaper 720 is preferably applied to a wearer by inserting the wearer's legs through the leg openings and then diaper 720 is pulled up over the wearer's buttocks.

It is herein contemplated and should be appreciated by one skilled in the art that the present invention may be applied to a pant (e.g., FIG. 8) and a non-preformed (e.g., FIG. 1) absorbent article. As such, all of the herein disclosed and foreseeable embodiments apply to both pant and non-preformed absorbent articles.

Figure 9:
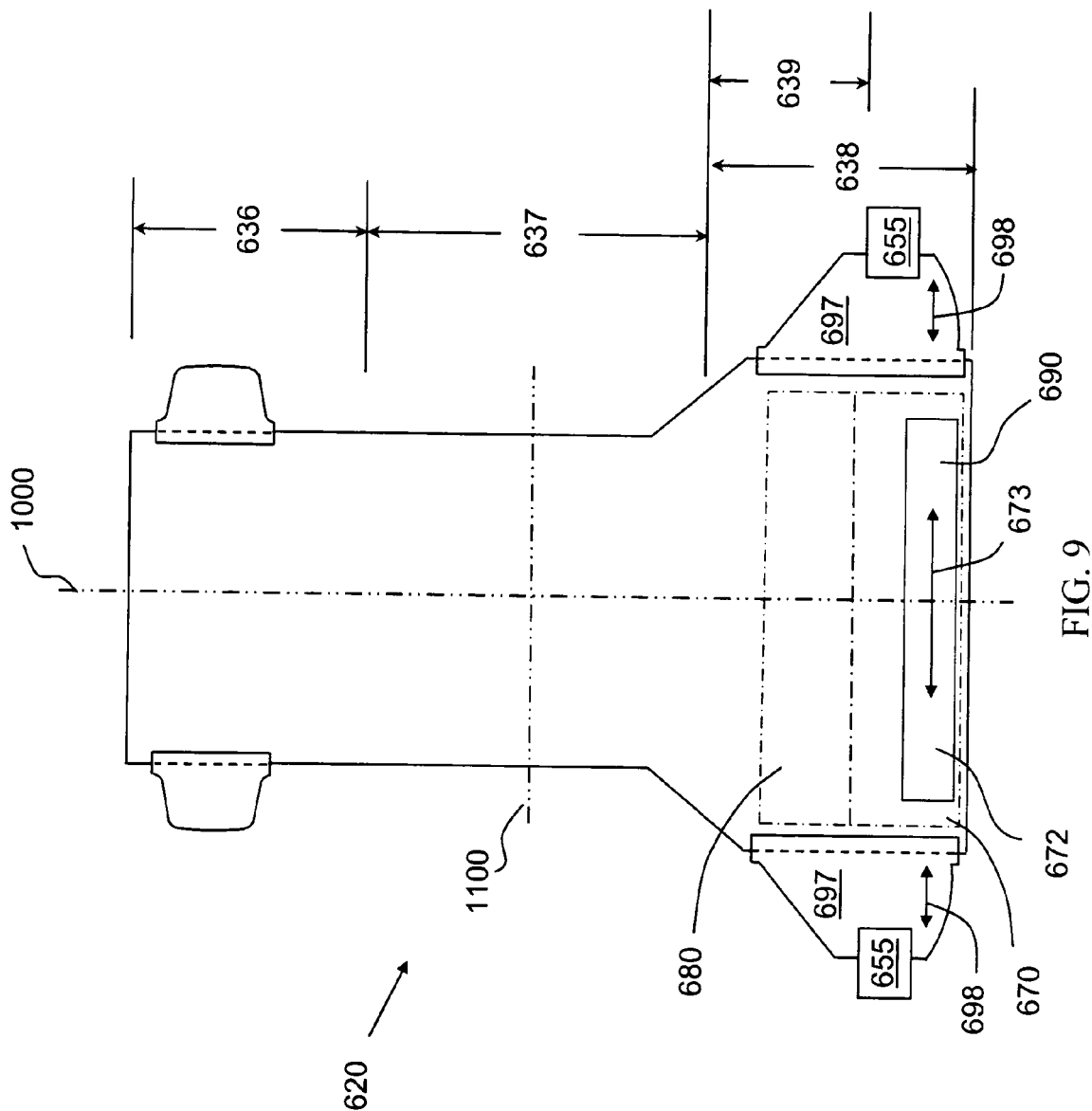
FIG. 9 is a plan view of the exemplary, non-limiting embodiment from FIG. 7.
Figure 10:
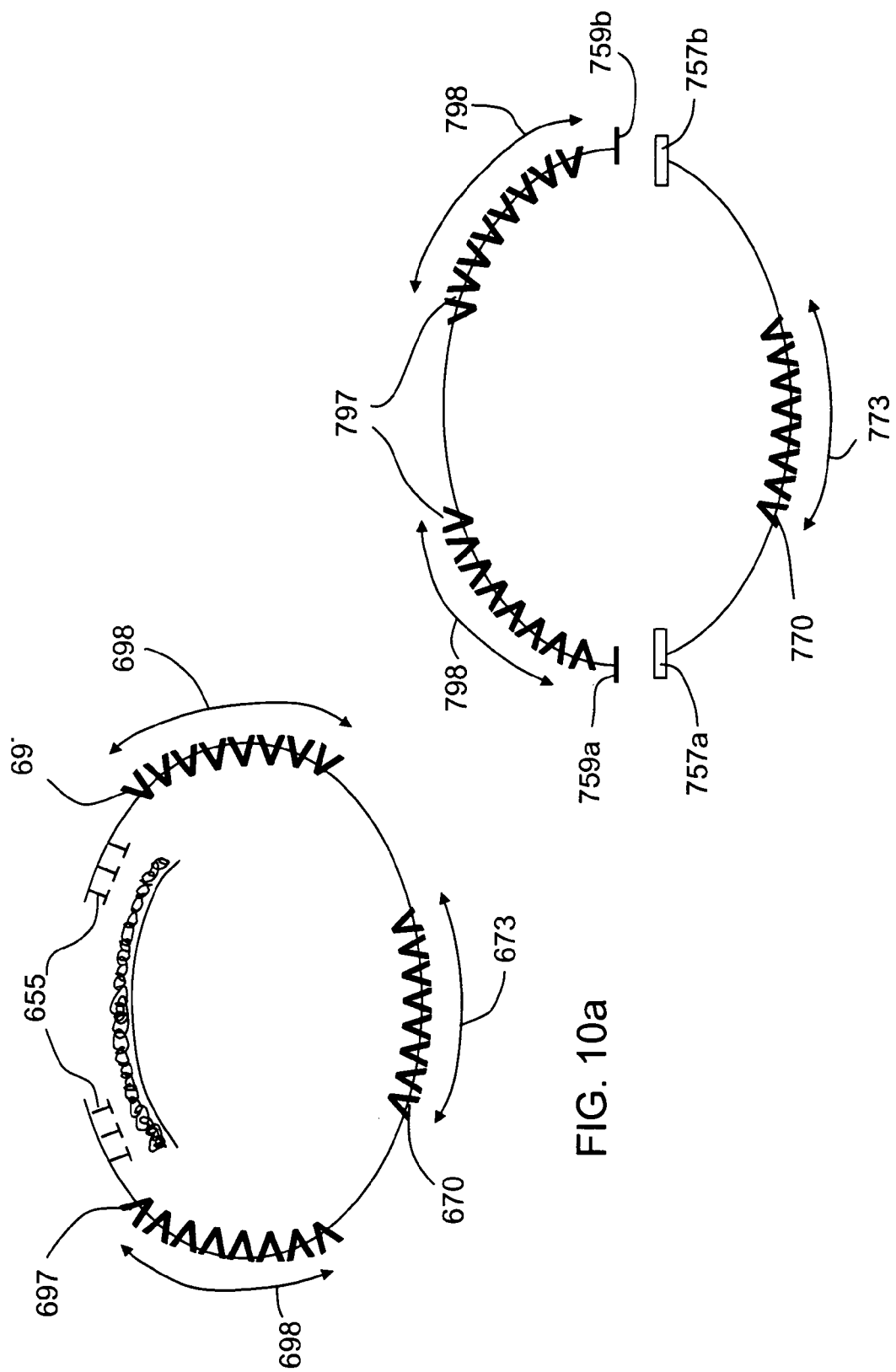
FIG. 10a is a schematic, cross-sectional view of the exemplary, non-limiting embodiment from FIG. 9 being worn as illustrated along line 10-10 in FIG. 11.
FIG. 10b is a schematic, cross-sectional view of the exemplary, non-limiting embodiment from FIG. 8 being worn as illustrated along line 10-10 in FIG. 11.

FIG. 9 is a plan view of the exemplary, non-limiting embodiment diaper 620 from FIG. 7. FIG. 10a is a schematic, cross-sectional view of diaper 620 from FIG. 9 being worn as illustrated along line 10-10 in FIG. 11. For purposes of FIG. 10a, diaper 620 is illustrated as a diaper having a front-fastened product execution which may or may not be preformed. Ears 697 are shown having stretch properties in the lateral direction as indicated by arrows 698. It has been discovered that diaper 620 provides better conformity and sustained fit when a first stretch region (e.g., second backsheet zone 670) having lateral stretch as indicated by vector 673 co-elongates with a second stretch region (e.g., ears 697) having lateral stretch as indicated by vector 698 under the same tensile force. In this way, the first stretch region (e.g., second backsheet zone 670) stretches and conforms to the wearer before the second stretch region (e.g., ears 697) is substantially stretched (i.e., stretched near its limit—that is, stretched near its maximum elongation); otherwise, the first region may wrinkle, gap, and/or begin to sag. In practical terms, when the caregiver applies diaper 620 with a given application tension, the first stretch region should co-elongate with the second stretch region instead of only beginning to elongate when the second stretch region is stretched near its limit. In preferred executions, under a laterally applied tensile load of between about 1 Newton and about 4 Newtons, the strain in the second stretch region is between at least about 10% and less than about 75%. Under the same tensile load, the strain the first stretch region is preferably greater than about 5%, more preferably greater than about 10%, and most preferably at least about equal to the strain in the second stretch region. The co-elongation exhibited between the first and second regions may be imparted through a variety of product design configurations/techniques including, but not limited to, (a) varying the longitudinal length and/or lateral width of the first and/or second stretch zone [e.g., longitudinally taller ears/side panels compared to a longitudinally shorter backsheet zone/stretch zone] and (b) varying the tensile modulus of the first and/or second stretch zone [e.g., the tensile modulus for the backsheet zone/stretch zone may be lower than the tensile modulus for the ears/side panels].

Similar to FIG. 10a, FIG. 10b shows a diaper having a side-fastened product execution which may or may not be preformed, wherein, a first stretch region (e.g., second backsheet zone 770) having lateral stretch as indicated by vector 773 co-elongates with a second stretch region (e.g., side panels 797) having lateral stretch 798 under the same tensile force. While the term "ears" is used herein when referring to non-pant diapers and the term "side panels" is used herein when referring to pant diapers, the two terms may be used herein interchangeably when appreciating the present invention.

Figure 11:
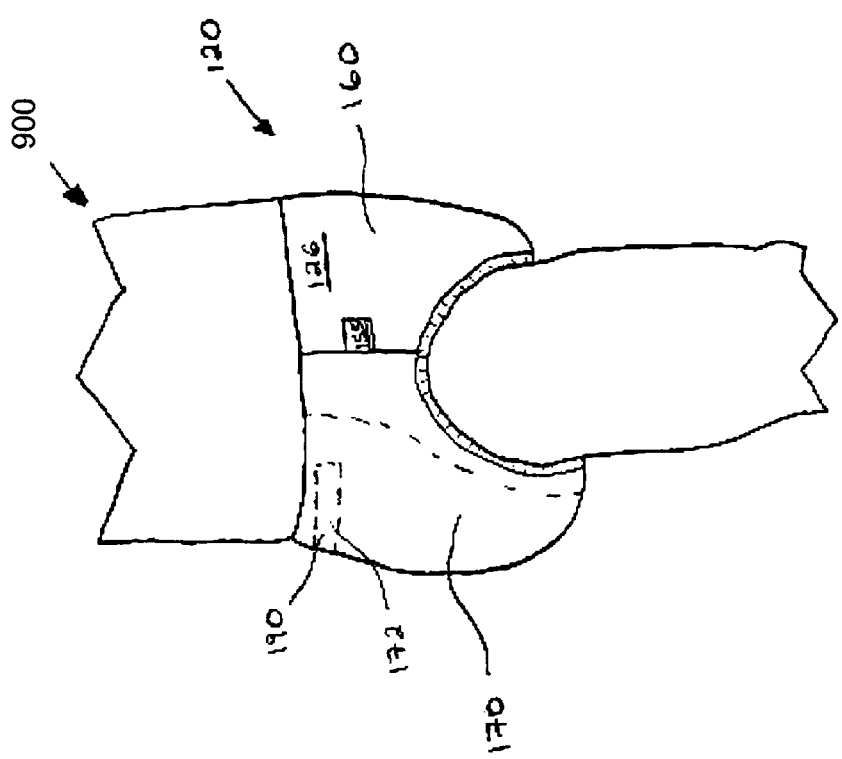
FIG. 11 is a side elevational view of the exemplary, non-limiting embodiment diaper from FIG. 2 being worn by a wearer.
Figure 12:
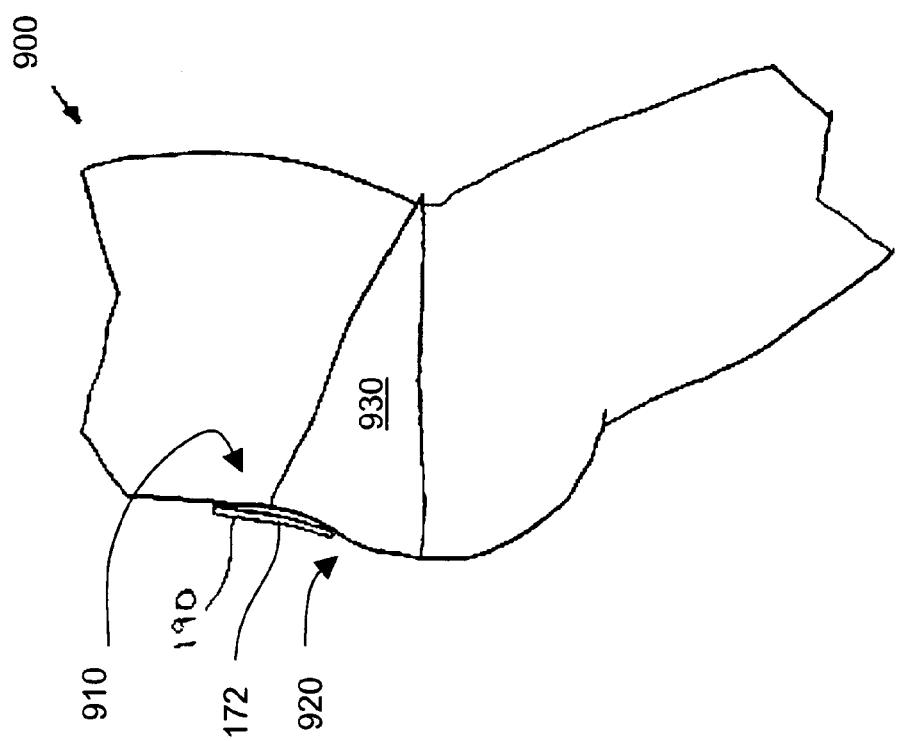
FIG. 12 is a schematic, side elevational view of the diaper in FIG. 11.

FIG. 11 is a side elevational view of the exemplary, non-limiting embodiment diaper 120 from FIG. 2 being worn by a wearer 900. As similarly illustrated in FIG. 2, backsheet 126, first backsheet zone 160, second backsheet zone 170, elastomeric element 190, stretch zone 172 and fastening element 155 are shown. FIG. 12 is a schematic, side elevational view of diaper 120 from FIG. 11. Referring now to both FIGS. 11 and 12, stretch zone 172 may be located at the back waist end 136 of diaper 120, located generally in the lower back waist area 910. In this way, the maximum fit and comfort will be experienced by wearer 900 as the tension is applied by diaper 120 to the wearer's body at or immediately above the convexity of the buttocks 920 (i.e., the buttocks "shelf"), contributing to the overall anchoring capability of diaper 120 (i.e., its ability to resist sagging). Said another way, stretch zone 172 operates to maintain diaper 120 in an optimal fit configuration with respect to the low motion zone 930 (i.e. the line or zone connecting the lumbar curve of the back over the hips to under the abdominal crease of a wearer's body 900) so as to maximize the performance thereof. For a more detailed discussion of low motion zones see U.S. Pat. No. 5,358,500.

Test Method for Measuring Elongation Force

1. Connect fastener components on one side of article (e.g., 759a and 757a in FIG. 10a). If article is a preformed pant, then break a connection on one side of article prior to testing.
2. Cut article along lateral axis 1100.
3. Make a pair of tick marks (i.e., indicia) within both the first stretch region and second stretch region. Measure the lateral gap for each pair of tick marks.
4. Grip opposing unconnected ends/fastening components in jaws at least as wide as the material being clamped. Grips should be attached such that a lateral tensile force can be applied to the first and second stretch regions between the jaws.
5. For a first test iteration, apply a 1 Newton tensile force, and then within about 15 seconds of applying said tensile force, measure the lateral gap for each pair of tick marks while the article is held in jaws.
6. For a second test iteration, apply a total of 2 Newton tensile force, and then within about 15 seconds of applying said tensile force, measure the lateral gap for each pair of tick marks while the article is held in jaws.
7. For a third test iteration, apply a total of 4 Newton tensile force, and then within about 15 seconds of applying said tensile force, measure the lateral gap for each pair of tick marks while the article is held in jaws.
8. Calculate Strain=$[100*(\text{Distance}_{(final)}-\text{Distance}_{(initial)})/\text{Distance}_{(initial)}]$ for first and second stretch regions for each test iteration.
9. Compare the strains of the first and second stretch regions. The following relationship should be true for at least one of the three test iterations:
    The first stretch region is said to co-elongate with the second stretch region when: (a) the strain in the second stretch region is between at least about 10% and less than about 75% and (b) the strain the first stretch region is preferably greater than about 5%, more preferably greater than about 10%, and most preferably at least about equal to the strain in the second stretch region.

The second region may be extensible or more preferably elastomeric. The second region may be located in any portion of the front waist region 636 or back waist region 638 including, but not limited to, a location near longitudinal centerline 1000 of said front waist region 636, laterally outboard from longitudinal centerline 1000 near one or both longitudinal edges 614 in either waist region, or in side panels 697 attached to one or more longitudinal edge 614 in one or more waist regions.

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

For example, one skilled in the art should appreciate that the present invention may also be incorporated into other wearable absorbent articles, such as catamenial and adult incontinence products, that encircle or enclose at least a portion of a wearer's anatomy or which are otherwise secured to a wearer.

One skilled in the art should also appreciate that the stretch zones may be parallel or nonparallel with respect to the lateral or longitudinal centerlines or with respect to each other. Additionally, the stretch zones may have different physical and/or elastic properties versus each other.

One skilled in the art should also appreciate that the elastomeric elements may be configured in any suitable shape including, but not limited to, linear and non-linear (e.g., substantially u-shaped, etc.).

While exemplary embodiments disclosed herein depicted the third backsheet zone having a lower basis weight, thickness, or density than the second backsheet zone which has a lower basis weight, thickness, or density than the first backsheet zone, one skilled in the art should also appreciate that second backsheet zone and/or first backsheet zone may have a lower physical property value than the third backsheet zone in some applications. For example, referring to FIG. 3, the second backsheet zone 270 (disposed primarily in the distal portion of the back waist region 238) may have a lower basis weight, thickness or density than that of the third backsheet zone 280 (disposed primarily in the buttock region 239). In this way, second backsheet zone 270 provides greater breathability (i.e., increased air permeability) than third backsheet zone 280 thus providing better dryness and comfort in the wearer's waist region; whereas, the third backsheet zone 280 is more adapted to ensure sufficient exudate containment. In another example, third backsheet zone 280 may have a lower basis weight, thickness or density than that of the second backsheet 270 in order to provide sufficient extension to enable pull-on application of the article (e.g., for pants).

While exemplary embodiments disclosed herein depict the second backsheet zone, for example, being positioned slightly away from the end edge 12 so as to provide less stretch for maintaining fit and shape, one skilled in the art would recognize that this gap (i.e., positioning away) may vary in length, including not existing.

While the physical properties of basis weight, thickness and density are discussed herein as methods for appreciating and measuring the present invention, one skilled in the art would recognize that tensile modulus may also sometimes be an acceptable physical property that may be measured to appreciate the present invention. Tensile modulus differences may be preferably measured with the backsheet strain between 0% and 5% elongation of the backsheet, or alternatively between 0% to 25%, or alternatively between 0% to 50%.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A unitary disposable absorbent article, comprising:
   an absorbent core having a garment-facing surface and a body-facing surface;
   a liquid permeable topsheet positioned adjacent said body-facing surface of said absorbent core;
   a liquid impermeable backsheet positioned adjacent said garment-facing surface of said absorbent core; said backsheet having a physical variation along a longitudinal axis of the article, wherein said physical variation defines a first backsheet zone and a second backsheet zone, wherein said physical variation is as measured by a physical property selected from the group consisting of at least one of basis weight, thickness and density; and
   at least one elastomeric element having at least one primary direction of stretch, said elastomeric element at least partially overlapping and joined to said second backsheet zone, wherein a relaxed pathlength of said elastomeric element in the primary direction of stretch is less than a total pathlength of said backsheet in the region of overlap.

2. The absorbent article of claim 1 wherein said first backsheet zone and said second backsheet zone partially overlap said longitudinal axis.

3. The absorbent article of claim 1 wherein said article further comprises:
   a front waist region;
   a back waist region, said front and back waist regions being located at opposite ends of said article, said front and back waist regions generally encircling a waist of a wearer when said article is worn;
   a crotch region, said crotch region being located intermediate to said front and back waist regions, said crotch region extending longitudinally between said front and back waist regions, said crotch region generally positioned between a pair of legs of a wearer; and
   a buttocks region, said crotch region being located intermediate to said front and back waist regions, said buttocks region being located near a proximal end of said back waist region,
   wherein said first backsheet zone is disposed primarily in said crotch region and said front waist region, wherein said second backsheet zone is at least partially disposed in said back waist region.

4. The absorbent article of claim 1 wherein said article further comprises:
   a front waist region;
   a back waist region, said front and back waist regions being located at opposite ends of said article, said front and back waist regions generally encircling a waist of a wearer when said article is worn;
   a crotch region, said crotch region being located intermediate to said front and back waist regions, said crotch region extending longitudinally between said front and back waist regions, said crotch region generally positioned between a pair of legs of a wearer; and
   a buttocks region, said crotch region being located intermediate to said front and back waist regions, said buttocks region being located near a proximal end of said back waist region,
   wherein said first backsheet zone is disposed primarily in said crotch region and said front waist region, wherein said second backsheet zone is at least partially disposed in said buttocks region.

5. The absorbent article of claim 4 wherein said elastomeric element is non-linear in shape.

6. The absorbent article of claim 1 wherein said physical variation is such that said second backsheet zone has a lower value than said first backsheet zone.

7. The absorbent article of claim 1 wherein said selected physical property is basis weight, wherein said physical variation is measured as a ratio such that said ratio of the basis weight of said second backsheet zone to the basis weight in said first backsheet zone is less than about 0.6.

8. The absorbent article of claim 1 wherein a ratio of the relaxed pathlength of said elastomeric element to a total pathlength of said backsheet within said second backsheet zone in a joined area is less than about 0.8.

9. The absorbent article of claim 1 further comprising a third backsheet zone having a value for said physical property that is different than a corresponding value for said first and second backsheet zone.

10. The absorbent article of claim 9 wherein said physical variation is such that said third backsheet zone has a higher value than said first backsheet zone and said second backsheet zone.

11. The absorbent article of claim 9 wherein said physical variation is such that said third backsheet zone has a higher value than said first backsheet zone and a lower value than said second backsheet zone.

12. The absorbent article of claim 9 wherein said third backsheet zone is at least partially disposed in said front waist region.

13. The absorbent article of claim 9 wherein said third backsheet zone is at least partially disposed in said buttocks region.

14. The absorbent article of claim 9 wherein said third backsheet zone is at least partially disposed in said back waist region.

15. The absorbent article of claim 9 further comprising a second elastomeric element at least partially overlapping and joined to said third backsheet zone, wherein a relaxed pathlength of said elastomeric element in the primary direction of stretch is less than a total pathlength of said backsheet in the region of overlap.

16. The absorbent article of claim 15 wherein said second elastomeric element is non-linear.

17. The absorbent article of claim 1 wherein said article may be selected from the group consisting of a disposable diaper, a catamenial and an adult incontinence product.

18. The absorbent article of claim 1 wherein said disposable diaper is a pant.

* * * * *